(12) United States Patent
Yamase et al.

(10) Patent No.: US 6,852,899 B2
(45) Date of Patent: Feb. 8, 2005

(54) PROCESS FOR PRODUCING ISOBUTYLENE AND METHANOL

(75) Inventors: Masanobu Yamase, Ichihara (JP); Yoshiaki Suzuki, Sodegaura (JP)

(73) Assignee: Sumitomo Chemical Company Limited, Osaka (JP)

(*) Notice: Subject to any disclaimer, the term of this patent is extended or adjusted under 35 U.S.C. 154(b) by 274 days.

(21) Appl. No.: 10/173,415

(22) Filed: Jun. 18, 2002

(65) Prior Publication Data
US 2003/0013933 A1 Jan. 16, 2003

(30) Foreign Application Priority Data

Jun. 21, 2001 (JP) ......................................... 2001-187923

(51) Int. Cl.[7] ............................................. C07C 1/213
(52) U.S. Cl. ........................................ 585/639; 585/640
(58) Field of Search ................................. 585/639, 640

(56) References Cited

U.S. PATENT DOCUMENTS

| 4,544,776 A | 10/1985 | Osterburg et al. |
| 6,072,095 A | 6/2000 | Marion et al. |
| 6,143,936 A | 11/2000 | Marion et al. |

FOREIGN PATENT DOCUMENTS

| GB | 1165479 | 10/1969 |
| GB | 1173128 | 12/1969 |
| GB | 1176620 | 1/1970 |
| GB | 1272585 | 5/1972 |
| JP | 47-41882 B | 10/1972 |
| JP | 3-45053 B | 7/1991 |

*Primary Examiner*—Thuan Dinh Dang
(74) *Attorney, Agent, or Firm*—Sughrue Mion, PLLC

(57) ABSTRACT

A process for producing isobutylene and methanol comprising: a first step of subjecting methyl-tert-butyl ether to decomposition in the presence of a catalyst to obtain a reaction liquid; a second step of washing the resultant with water to separate the reaction liquid into an oil layer and an aqueous layer; a third step of subjecting the oil layer to distillation to obtain a fraction containing isobutylene and a dialkyl ether from the top of a distillation column, a fraction containing methyl-tert-butyl ether and the heavy components from the bottom of the column and a fraction containing methyl-tert-butyl ether from a side cut of the column, and recycling the side cut fraction to the first step; and a fourth step of subjecting the aqueous layer to distillation to obtain a fraction containing methanol from the top of a distillation column and a fraction containing water from the bottom of the column.

3 Claims, 1 Drawing Sheet

PROCESS FOR PRODUCING ISOBUTYLENE AND METHANOL

BACKGROUND OF THE INVENTION

1. Technical Field

The present invention relates to a process for producing isobutylene and methanol. More particularly, the present invention relates to a process for producing isobutylene and methanol in which methyl-tert-butyl ether is decomposed into isobutylene and methanol, and isobutylene and methanol are separated, followed by recovering them individually, thereby providing a process which can obtain isobutylene and methanol in economical characterized by suppressing losses of methyl-tert-butyl ether as a raw material.

2. Description of Related Arts

A method of recovering isobutylene and methanol by decomposing methyl-tert-butyl ether into isobutylene and methanol and separating isobutylene and methanol respectively therefrom is known (e.g. JP47-041882B). However, according to this method, heavy components such as isobutylene dimer and trimer and the like formed as by-products in the first step are concentrated, and as the result, the activity of a methyl-tert-butyl ether decomposition catalyst markedly decreases.

On the other hand, when a part thereof is withdrawn for avoiding the concentration of these heavy components, methyl tert-butyl ether as a row material is accompanied therewith, and therefore, there was a problem such disadvantages in economical.

SUMMARY OF THE INVENTION

An object of the present invention is to provide a process for producing isobutylene and methanol, comprising decomposing methyl-tert-butyl ether into isobutylene and methanol to obtain a mixture thereof, separating isobutylene and methanol therefrom to recover isobutylene and methanol individually, the process suppressing a loss of methyl-tert-butyl ether, thereby being capable of obtaining isobutylene and methanol in economical.

Namely, the present invention relates to a process for producing isobutylene and methanol comprising decomposing methyl-tert-butyl ether into isobutylene and methanol to obtain a mixture containing isobutylene and methanol, separating isobutylene and methanol therefrom thereby to recover isobutylene and methanol individually, wherein the process comprising the following steps:

a first step of subjecting methyl-tert-butyl ether to decomposition reaction in the presence of a solid acid catalyst to obtain a reaction liquid containing isobutylene, methanol and, as by-products, a dialkyl ether and heavy components containing an isobutylene dimer and an isobutylene trimer;

a second step of washing the reaction liquid obtained in the first step with water to separate the reaction liquid into an oil layer and an aqueous layer;

a third step of subjecting the oil layer obtained in the second step to distillation using a distillation column to obtain a fraction containing isobutylene and the dialkyl ether from a top of the distillation column, a fraction containing methyl-tert-butyl ether and the heavy components from a bottom of the distillation column and a fraction containing methyl-tert-butyl ether from a side cut of the distillation column, and recycling the fraction obtained from the side cut to the first step; and a fourth step of subjecting the aqueous layer obtained in the second step to distillation using a distillation column to obtain a fraction containing methanol from a top of the distillation column and a fraction containing water from a bottom of the distillation column.

EXPLANATION OF SYMBOLS

Figure 1:
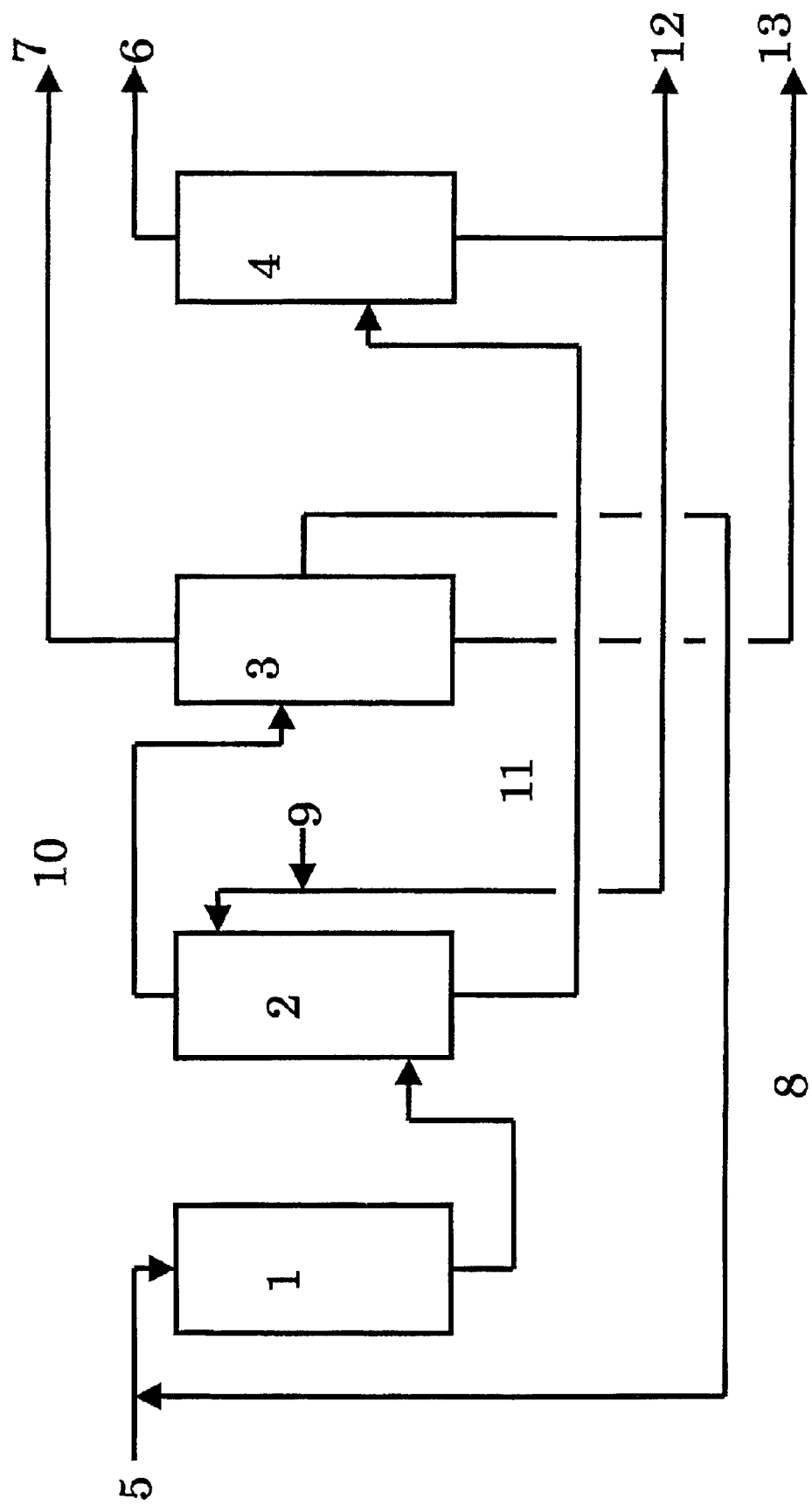
FIG. 1 shows a flow of an example of a production process according to the present invention.

1. First step, 2. Second step, 3. Third step, 4. Fourth step 5. Methyl tert-butyl ether (raw material for decomposition), 6. Methanol (objective product), 7. Isobutylene (objective product), 8. Side cut(recycled), 9. Washing water, 10. Oil layer 11. Water layer, 12. Waste water, 13. Fraction containing Methyl tert-butyl ether and heavy components

DETAILED DESCRIPTION OF THE INVENTION

The first step in the present invention is a step of subjecting methyl-tert-butyl ether to a decomposition reaction in the presence of a solid acid catalyst to obtain isobutylene, methanol, and, as by-products, a dialkyl ether and heavy components containing an isobutylene dimer and an isobutylene trimer. Conditions and specific examples of the first step include the followings.

In the first step, a solid acid catalyst, for example, an alumina-modified silica is usually used.

A gas phase reaction of fixed bed is usually adopted in the first step, the reaction temperature is usually from 150 to 300° C. and the reaction pressure is usually from an ordinary pressure to 10 kg/cm$^2$G. A feed rate of a raw material is selected depending on the reaction temperature, the reaction pressure, a conversion of desired methyl-tert-butyl ether or the like, and usually from 3 to 20 (h$^{-1}$) in terms of liquid hourly space velocity (LHSV). The reaction gas is liquefied after cooled in a heat recovery equipment.

In the second step of the present invention, the reaction liquid obtained in the first step is washed with water and then separated into an oil layer and an aqueous layer. Conditions and specific examples of the second step include the followings.

In the second step, any types of extraction column such as a sieve tray type column and a rotary disk type column can be used. An operation pressure is usually from 6 to 8 kg/cm$^2$G since it is controlled at the liquid phase. A weight ratio of the washing water/oil is usually from about 0.4 to 0.8, preferably from 0.4 to 0.6. In addition, a part or whole of water drawn from the bottom of the column in the fourth step may be recovered to be reused as the washing water.

In the third step, the oil layer obtained in the second step is subjected to distillation to obtain a fraction containing isobutylene and a dialkyl ether from a top of a distillation column, a fraction containing methyl-tert-butyl ether and heavy components from a bottom of the distillation column and a fraction containing methyl-tert-butyl ether from a side cut of the distillation column, and the fraction obtained from the side cut is recycled to the first step. Conditions and specific examples of the third step include the followings.

In the third step, an ordinary distillation column such as a sieve tray type column, a valve tray type column or a packed column can be used in the third step. The operation pressure is a pressure enough to condense the overhead of the column by cooling water of a temperature usually used, and usually from 4 to 6 kg/cm$^2$G.

The side cut liquid is withdrawn from a plate in which a fraction of distillate of the top of the column is not contained and a content of heavy components is sufficiently small, that is, from any of 2nd to 5th plates in a theoretical plate number from the bottom of the column, and the amount of the side cut depends on a conversion of methyl-tert-butyl ether and is usually determined so that the concentration of methyl tert-butyl ether in the fraction of the bottom of the column becomes about 20 to about 60% by weight.

In the fourth step of the present invention, the water layer obtained in the second step is subjected to a distillation to obtain a methanol fraction from a top of a distillation column and a fraction containing water from a bottom of the distillation column.

Conditions and specific examples of the present step include the followings.

An ordinary distillation column such as a sieve tray type column, a valve tray type column or a packed column can be used in the fourth step.

An operation pressure is usually from an atmospheric pressure to 0.3 kg/cm$^2$G.

The most significant characteristic of the present process is to obtain the fraction containing methyl tert-butyl ether from the side cut of the distillation column in the third step and to recycle the fraction obtained from the side cut to the first step.

By adopting this process, the amount of methyl tert-butyl ether lost from the bottom of the column can be reduced and it can be reused as a raw material for decomposition.

On the other hand, not according to the present invention, when the second and third steps are changed in order, that is, the reaction product obtained in the first step is subjected to distillation to obtain isobutylene, a dialkyl ether and a small amount of azeotropic methanol from the top of the distillation column and methanol, methyl tert-butyl ether and heavy components from the bottom of the column, the fraction from the top of the column is subjected to washing with water to eliminate methanol and water containing methanol after the washing is subjected to distillation to recover methanol, there is occurred troublesomeness that water formed with generation of a dialkyl ether as a by-product in the first step in a fraction of distillate of the bottom of the column obtained by subjecting the reaction product to distillation, is contained.

Further, as disclosed in JP02-031695B, when water or steam is added in the first step, it is impossible to directly recycle a fraction of distillate of the bottom of the column for synthesizing methyl tert-butyl ether because this water is contained therein.

Therefore, it is necessary to separate water from said fraction, further, because methyl tert-butyl ether, heavy components and the like are contained in methanol recovered by eliminating water, a separation treatment thereof is required and leads to remarkable disadvantages.

EXAMPLE

Example 1 and Comparative Example 1

As shown in a flow of FIG. 1, the following first to fourth steps were employed in Example 1.

Abbreviations in tables are as follows:
MTBE: methyl-tert-butyl ether;
DIB: isobutylene dimer;
DME: dialkyl ether; and
TBA: tert-butanol.

First Step: Methyl-tert-butyl ether was subjected to a decomposition reaction in the presence of an alumina-containing solid acid catalyst to obtain isobutylene, methanol and dialkyl ether and heavy components including an isobutylene dimer and an isobutylene trimer as by-products. A fixed bed gaseous phase reaction was adopted. The reaction temperature was 220° C., and the reaction pressure was 6 kg/cm$^2$G. The feed rate of the methyl tert-butyl ether was 3 (h$^{-1}$) at LHSV. The reaction gas was liquefied after cooled by a heat recovery equipment.

Second Step: The reaction liquid obtained in the first step was washed with water to be separated into an oil layer and an aqueous layer. A sieve tray type column was used for the washing, wherein the operation pressure was set to 7 kg/cm$^2$G at a top of the column and the weight ratio of the washing water/oil was set to 0.45.

Third Step: The oil layer obtained in the second step was subjected to distillation to obtain a fraction containing isobutylene and dialkyl ether from a top of a distillation column, a fraction containing methyl-tert-butyl ether and heavy components from a bottom of the distillation column and a fraction containing methyl-tert-butyl ether (containing a small amount of heavy components) from the side cut, and the fraction obtained from the side cut was recycled to the first step.

Fourth Step: The aqueous layer obtained in the second step was subjected to a distillation to obtain a fraction containing methanol from a top of a distillation column as well as a fraction containing water from a bottom of the distillation column. A valve tray type column was used for the distillation, and the operation pressure was set to 0.25 kg/cm$^2$G.

In Comparative Example 1, withdrawal of side cut in the third step was not carried out. The consumption of MTBE [converted to Gloss (MTBE-ton/isobutylene-ton)] became 1.688.

Results in Comparative Example 1 are shown in the following tables. Numerical values in the tables are in % by weight.

TABLE 1

First Step

|  | Feed | Reaction Effluent |
|---|---|---|
| MTBE | 95 | 4.3 |
| DIB | 0.7 | 0.9 |
| Water | 2.9 | 3.1 |
| Isobutylene | 0.0 | 57.9 |
| Methanol | 0.1 | 32.8 |
| DME | 0.0 | 0.2 |

TABLE 2

Second Step

|  | Oil layer after washing | Water layer after washing |
|---|---|---|
| MTBE | 6.3 | 0.4 |
| DIB | 1.5 | 0.0 |
| Water | 0.1 | 60.0 |
| Isobutylene | 90.9 | 0.8 |
| Methanol | 0.0 | 38.6 |
| DME | 0.3 | 0.0 |

TABLE 3

Third Step

| | Effluent from column top | Effluent from column bottom |
|---|---|---|
| MTBE | 0.0 | 73.0 |
| DIB | 0.0 | 17.3 |
| Water | 0.1 | 0.0 |
| Isobutylene | 99.5 | 0.1 |
| Methanol | 0.0 | 0.0 |
| DME | 0.3 | 0.0 |

TABLE 4

Fourth Step

| | Effluent from column top | Effluent from column bottom |
|---|---|---|
| MTBE | 1.0 | 0.0 |
| DIB | 0.0 | 0.0 |
| Water | 0.1 | 99.7 |
| Isobutylene | 1.9 | 0.0 |
| Methanol | 96.9 | 0.3 |
| DME | 0.0 | 0.0 |

On the other hand, Example 1 was conducted according to the above-mentioned procedure. In addition, the withdrawal of the side cut from 4th theoretical column from the bottom of the 10 column in the third step was carried out. The amount of the side cut was withdrawn so that the concentration of MTBE in the effluent from the column bottom in Table 3 of Comparative Example 1 become 60 t by weight, and whole of the side cut was recycled to the first step.

As results, the consumption of MTBE (converted to Gloss (MTBE-ton/isobutylene-ton) became 1.654, and it decreased compared to Comparative Example 1.

As described above, the present invention provides a process for producing isobutylene and methanol in which methyl-tert-butyl ether is decomposed into isobutylene and methanol, and isobutylene and methanol are separated, followed by recovering them individually, thereby providing a process which can obtain isobutylene and methanol in economical characterized by suppressing losses of methyl-tert-butyl ether as a raw material.

What is claimed is:

1. A process for producing isobutylene and methanol comprising decomposing methyl-tert-butyl ether into isobutylene and methanol to obtain a mixture containing isobutylene and methanol, separating isobutylene and methanol therefrom, thereby individually recovering isobutylene and methanol, wherein the process comprising the following steps:

a first step of subjecting methyl-tert-butyl ether to a decomposition reaction in the presence of a solid acid catalyst to obtain a reaction liquid containing isobutylene, methanol and, as by-products, a dialkyl ether and heavy components containing an isobutylene dimer and an isobutylene trimer;

a second step of washing the reaction liquid obtained in the first step with water to separate the reaction liquid into an oil layer and an aqueous layer;

a third step of subjecting the oil layer obtained in the second step to distillation using a distillation column to obtain a fraction containing isobutylene and the dialkyl ether from a top of the distillation column, a fraction containing methyl-tert-butyl ether and the heavy components from a bottom of the distillation column and a fraction containing methyl-tert-butyl ether from a side cut of the distillation column, and recycling the fraction obtained from the side cut to the first step; and a fourth step of subjecting the water layer obtained in the second step to distillation using a distillation column to obtain a fraction containing methanol from a top of the distillation column and a fraction containing water from a bottom of the distillation column.

2. The process according to claim 1, wherein the amount of the fraction withdrawn from the side cut is set to an amount so that the concentration of methyl-tert-butyl ether contained in the fraction from the bottom of the column in the third step becomes about 20 to about 60% by weight.

3. The process according to claim 1, wherein the fraction from the side cut is withdrawn from any of 2nd to 5th plates in theoretical plate number from the bottom of the column.

* * * * *